United States Patent
Takahashi

(10) Patent No.: US 11,922,603 B2
(45) Date of Patent: Mar. 5, 2024

(54) RADIOGRAPHIC IMAGE PROCESSING DEVICE, RADIOGRAPHIC IMAGE PROCESSING METHOD, AND RADIOGRAPHIC IMAGE PROCESSING PROGRAM

(71) Applicant: FUJIFILM Corporation, Tokyo (JP)

(72) Inventor: Tomoyuki Takahashi, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 272 days.

(21) Appl. No.: 17/387,480

(22) Filed: Jul. 28, 2021

(65) Prior Publication Data

US 2022/0036519 A1    Feb. 3, 2022

(30) Foreign Application Priority Data

Jul. 31, 2020    (JP) ................. 2020-130629

(51) Int. Cl.

| | | |
|---|---|---|
| G06K 9/00 | (2022.01) | |
| A61B 6/00 | (2006.01) | |
| G06T 5/00 | (2006.01) | |
| G06T 5/20 | (2006.01) | |
| G06T 5/50 | (2006.01) | |

(52) U.S. Cl.
CPC ............ G06T 5/003 (2013.01); A61B 6/5235 (2013.01); A61B 6/5258 (2013.01); G06T 5/008 (2013.01);
(Continued)

(58) Field of Classification Search
CPC . G06T 5/002; G06T 2207/20192; G06T 5/20; G06T 5/008; G06T 5/003;
(Continued)

(56) References Cited

U.S. PATENT DOCUMENTS

2010/0027867 A1* 2/2010 Bernhardt ............ A61B 6/4035
378/62
2011/0305405 A1    12/2011 Kawamura
(Continued)

FOREIGN PATENT DOCUMENTS

| JP | 2002-133410 A | | 5/2002 |
| JP | 2005021456 A | * | 1/2005 |

(Continued)

OTHER PUBLICATIONS

"Notice of Reasons for Refusal" Office Action issued in JP 2020-130629; mailed by the Japanese Patent Office dated May 30, 2023.

*Primary Examiner* — Emily C Terrell
*Assistant Examiner* — Kevin M Coomber
(74) *Attorney, Agent, or Firm* — Studebaker & Brackett PC

(57) ABSTRACT

A processor acquires a first radiographic image and a second radiographic image that include the same subject and have different S/N ratios. The processor derives a processing content of a first graininess suppression process on the first radiographic image having a higher S/N ratio of the first radiographic image and the second radiographic image and derives a processing content of a second graininess suppression process on the second radiographic image on the basis of the processing content of the first graininess suppression process. The processor performs a graininess suppression process on the second radiographic image on the basis of the processing content of the second graininess suppression process.

10 Claims, 7 Drawing Sheets

(52) U.S. Cl.
CPC ............... *G06T 5/20* (2013.01); *G06T 5/50* (2013.01); *G06T 2207/10116* (2013.01); *G06T 2207/20192* (2013.01)

(58) Field of Classification Search
CPC ... G06T 7/11; G06T 5/50; G06T 2207/10116; A61B 6/5258; A61B 6/5217; A61B 6/4266; A61B 6/4241; A61B 6/5235; H04N 5/3205
See application file for complete search history.

(56) References Cited

U.S. PATENT DOCUMENTS

| | | | |
|---|---|---|---|
| 2014/0314333 A1* | 10/2014 | Takahashi | A61B 6/5258 382/264 |
| 2016/0140720 A1 | 5/2016 | Naito | |
| 2016/0354052 A1 | 12/2016 | Kawanishi | |
| 2018/0061088 A1* | 3/2018 | Bhagalia | G06T 11/003 |
| 2018/0068422 A1* | 3/2018 | Kawamura | G06T 5/50 |
| 2018/0293715 A1* | 10/2018 | Kawamura | A61B 6/4266 |
| 2019/0223820 A1* | 7/2019 | Nemoto | A61B 6/5282 |
| 2019/0374184 A1 | 12/2019 | Takahashi | |

FOREIGN PATENT DOCUMENTS

| | | | |
|---|---|---|---|
| JP | 2008272476 A | | 11/2008 |
| JP | 2011-255060 A | | 12/2011 |
| JP | 2014151009 A | * | 8/2014 |
| JP | 2015-043959 A | | 3/2015 |
| JP | 2015-167613 A | | 9/2015 |
| JP | 2017074452 A | | 4/2017 |
| JP | 2019115545 A | | 7/2019 |
| JP | 2019-209027 A | | 12/2019 |

\* cited by examiner

RADIOGRAPHIC IMAGE PROCESSING DEVICE, RADIOGRAPHIC IMAGE PROCESSING METHOD, AND RADIOGRAPHIC IMAGE PROCESSING PROGRAM

CROSS REFERENCE TO RELATED APPLICATIONS

The present application claims priority under 35 U.S.C. § 119 to Japanese Patent Application No. 2020-130629 filed on Jul. 31, 2020. The above application is hereby expressly incorporated by reference, in its entirety, into the present application.

BACKGROUND

Technical Field

The present disclosure relates to a radiographic image processing device, a radiographic image processing method, and a radiographic image processing program.

Related Art

In the related art, an energy subtraction process is known which uses two radiographic images obtained by irradiating a subject with two types of radiation having different energy distributions, using the fact that the amount of attenuation of the transmitted radiation varies depending on a substance constituting the subject. The energy subtraction process is a method which makes pixels of the two radiographic images obtained as described above correspond to each other, multiplies the corresponding pixels by an appropriate weighting coefficient, and performs subtraction to acquire an image obtained by extracting a specific structure. In a case in which the energy subtraction process is performed to derive a soft part image obtained by extracting a soft part from, for example, the radiographic image of the chest, it is possible to observe shadows that appear in the soft part without being disturbed by a bone part. On the contrary, in a case in which a bone part image obtained by extracting a bone part is derived, it is possible to observe shadows that appear in the bone part without being disturbed by the soft part.

A one-shot method and a two-shot method are known as an imaging method for performing the energy subtraction process (hereinafter, referred to as an energy subtraction imaging method). In the one-shot method, two radiation detectors that detect radiation to acquire radiographic images are stacked with a radiation energy conversion filter interposed therebetween. Then, the two radiation detectors which are stacked are irradiated with radiation transmitted through the subject at the same time. Therefore, the two radiation detectors are irradiated with the radiation having different energy distributions. The two-shot method is a method which performs imaging twice using two types of radiation having different energy distributions.

On the other hand, the radiographic image has a problem that graininess deteriorates due to the influence of the quantum noise of radiation (hereinafter, simply referred to as noise) in a portion in which the dose of radiation is low and density is low. For this reason, various methods have been proposed which perform a process for suppressing graininess in the radiographic image as image processing on the radiographic image. For example, a method has been proposed which estimates the amount of noise included in a radiographic image, converts the amount of noise on the basis of body thickness information, and removes the noise of the radiographic image on the basis of the amount of converted noise to suppress graininess (see, for example, JP2015-167613A).

A smoothing process using a smoothing filter that removes a frequency component corresponding to noise is well known as a graininess suppression process. For example, JP2002-133410A discloses a method which performs frequency conversion on a radiographic image to create a band image indicating frequency components in different frequency bands, detects an edge direction of the pixel of interest to be processed in the band image, performs a smoothing process along the edge direction, and performs frequency synthesis on the band image subjected to the smoothing process to acquire a processed radiographic image. The performance of the graininess suppression process makes it possible to reduce graininess while preserving the edge included in the radiographic image.

However, in the one-shot method of the energy subtraction imaging, two radiation detectors which are stacked with a radiation energy conversion filter interposed therebetween are irradiated with the radiation transmitted through the subject at the same time. Therefore, the radiation detector that is farther away from a radiation source is irradiated with a lower dose of radiation than the radiation detector closer to the radiation source. In addition, in the case of the two-shot method, the dose of radiation in a second imaging operation is lower than the dose of radiation in a first imaging operation in order to reduce the dose of exposure to the subject. Therefore, of two radiographic images acquired by the energy subtraction process, one radiographic image has a larger amount of noise than the other radiographic image (that is, a signal-to-noise ratio (S/N ratio) is low). In this case, smoothing is performed on the radiographic image along the edge direction as described above to suppress graininess while preserving the edge included in the radiographic image.

However, in a radiographic image having a large amount of noise (hereinafter, referred to as a radiographic image with a low S/N ratio), the amplitude of the signal value of the noise to be removed may be larger than the contrast of the edge to be preserved. Therefore, in a case in which the graininess suppression process is performed on the radiographic image with a low S/N ratio, noise can be suppressed, but the contrast of the edge is reduced. As a result, since it is difficult to achieve both the suppression of noise and the preservation of the edge, the edge is buried in noise. Therefore, it is difficult to restore a structure such as the edge included in the radiographic image.

SUMMARY OF THE INVENTION

The present disclosure has been made in view of the above-mentioned problems, and an object of the present disclosure is to appropriately suppress the graininess of a radiographic image with a low S/N ratio.

According to an aspect of the present disclosure, there is provided a radiographic image processing device comprising at least one processor. The processor is configured to: acquire a first radiographic image and a second radiographic image that include the same subject and have different S/N ratios; derive a processing content of a first graininess suppression process on the first radiographic image having a higher S/N ratio of the first radiographic image and the second radiographic image; derive a processing content of a second graininess suppression process on the second radiographic image on the basis of the processing content of the first graininess suppression process; and perform a graininess suppression process on the second radiographic image on the basis of the processing content of the second graininess suppression process.

In addition, in the radiographic image processing device according to the aspect of the present disclosure, the processing content of the second graininess suppression process performed on each pixel of the second radiographic image may be the same as the processing content of the first graininess suppression process performed on each pixel of the first radiographic image corresponding to each pixel of the second radiographic image.

Further, in the radiographic image processing device according to the aspect of the present disclosure, the processor may be configured to derive a processing region, in which the first graininess suppression process is performed on a pixel of interest, as the processing content of the first graininess suppression process on the basis of a difference between a pixel value of the pixel of interest and a pixel value of a pixel around the pixel of interest in the first radiographic image.

Furthermore, in the radiographic image processing device according to the aspect of the present disclosure, the processor may derive a weight for a pixel in the processing region as the processing content of the first graininess suppression process on the basis of the difference.

Further, in the radiographic image processing device according to the aspect of the present disclosure, the processing content may be a filter characteristic of an edge-preserving smoothing filter.

Further, in the radiographic image processing device according to the aspect of the present disclosure, the processor may be configured to: derive a physical quantity map of the subject on the basis of at least one of the first radiographic image or the second radiographic image; and derive the processing content of the first graininess suppression process on the basis of the physical quantity map.

Further, in the radiographic image processing device according to the aspect of the present disclosure, the first radiographic image and the second radiographic image may be acquired on the basis of radiation that is for energy subtraction and has different energy distributions.

According to another aspect of the present disclosure, there is provided a radiographic image processing method comprising: acquiring a first radiographic image and a second radiographic image that include the same subject and have different S/N ratios; deriving a processing content of a first graininess suppression process on the first radiographic image having a higher S/N ratio of the first radiographic image and the second radiographic image; deriving a processing content of a second graininess suppression process on the second radiographic image on the basis of the processing content of the first graininess suppression process; and performing a graininess suppression process on the second radiographic image on the basis of the processing content of the second graininess suppression process.

In addition, a program that causes a computer to perform the radiographic image processing method according to the aspect of the present disclosure may be provided.

According to the present disclosure, it is possible to appropriately suppress the graininess of a radiographic image with a low S/N ratio.

DETAILED DESCRIPTION

Figure 1:
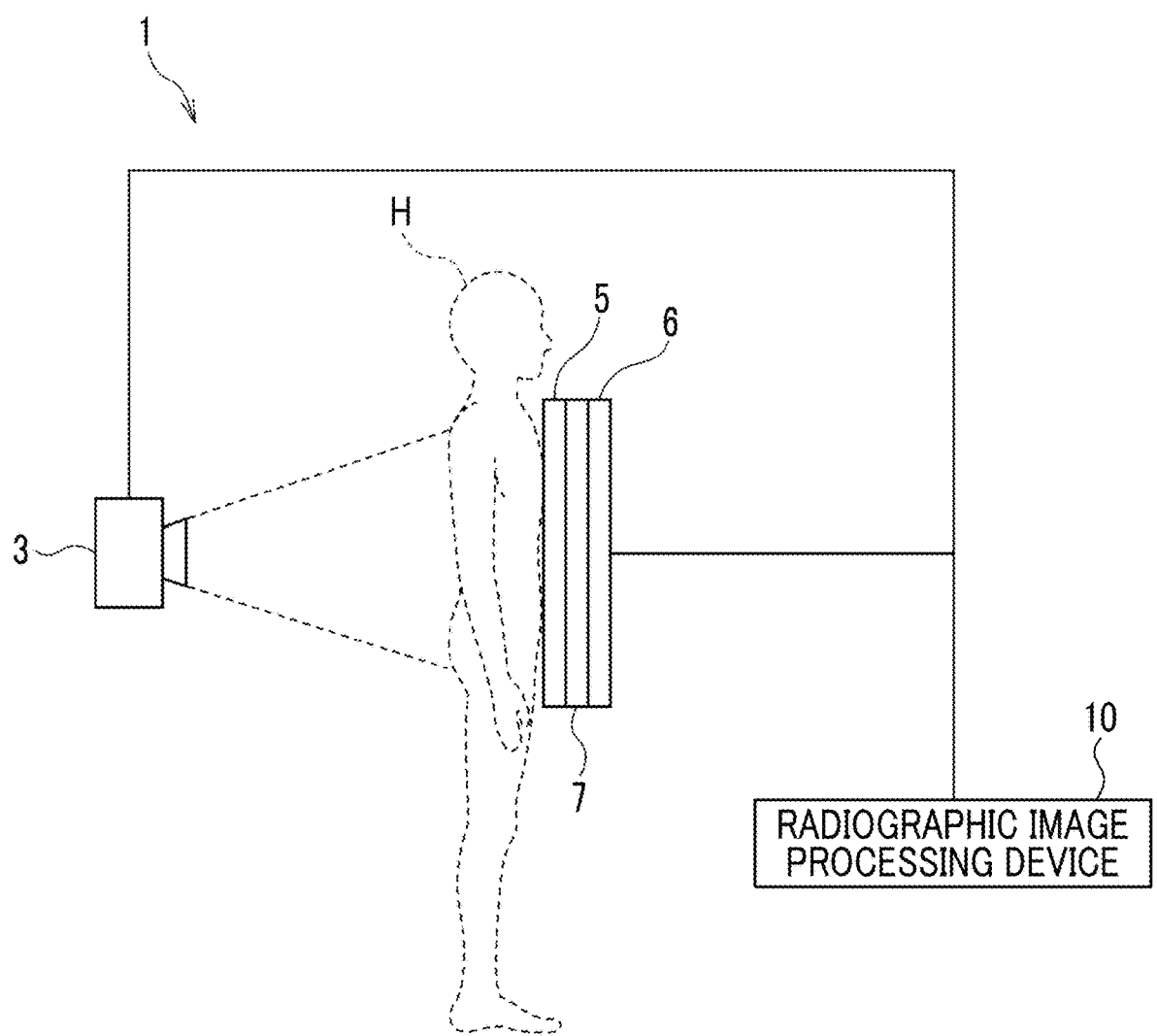
FIG. 1 is a diagram schematically illustrating a configuration of a radiography system to which a radiographic image processing device according to a first embodiment of the present disclosure is applied.

Hereinafter, embodiments of the present disclosure will be described with reference to the drawings. FIG. 1 is a block diagram schematically illustrating a configuration of a radiography system to which a radiographic image processing device according to a first embodiment of the present disclosure is applied. As illustrated in FIG. 1, the radiography system according to this embodiment comprises an imaging apparatus 1 and a radiographic image processing device 10 according to this embodiment.

The imaging apparatus 1 performs energy subtraction using a so-called one-shot method that irradiates a first radiation detector 5 and a second radiation detector 6 with radiation, such as X-rays which have been emitted from a radiation source 3 and transmitted through a subject H, while changing energy. At the time of imaging, as illustrated in FIG. 1, the first radiation detector 5, a radiation energy conversion filter 7 that consists of, for example, a copper plate, and the second radiation detector 6 are disposed in this order from the side closer to the radiation source 3, and the radiation source 3 is driven. In addition, the first and second radiation detectors 5 and 6 and the radiation energy conversion filter 7 come into close contact with each other.

With this configuration, the first radiation detector 5 acquires a first radiographic image G1 of the subject H obtained by low-energy radiation including so-called soft rays. Further, the second radiation detector 6 acquires a second radiographic image G2 of the subject H obtained by high-energy radiation excluding soft rays. The first and second radiographic images are input to the radiographic image processing device 10. Both the first radiographic image G1 and the second radiographic image G2 are front images including the chest and abdomen of the subject H.

The first and second radiation detectors 5 and 6 can repeatedly perform the recording and reading of a radiographic image and may be a so-called direct-type radiation detector that directly receives the emitted radiation and generates charge or a so-called indirect-type radiation detector that converts radiation into visible light and then converts the visible light into a charge signal. In addition, as a method for reading a radiographic image signal, it is desirable to use a so-called thin film transistor (TFT) reading method which turns on and off a TFT switch to read a radiographic image signal or a so-called optical reading method which emits reading light to read a radiographic image signal. However, the present disclosure is not limited thereto and other methods may be used.

Figure 2:
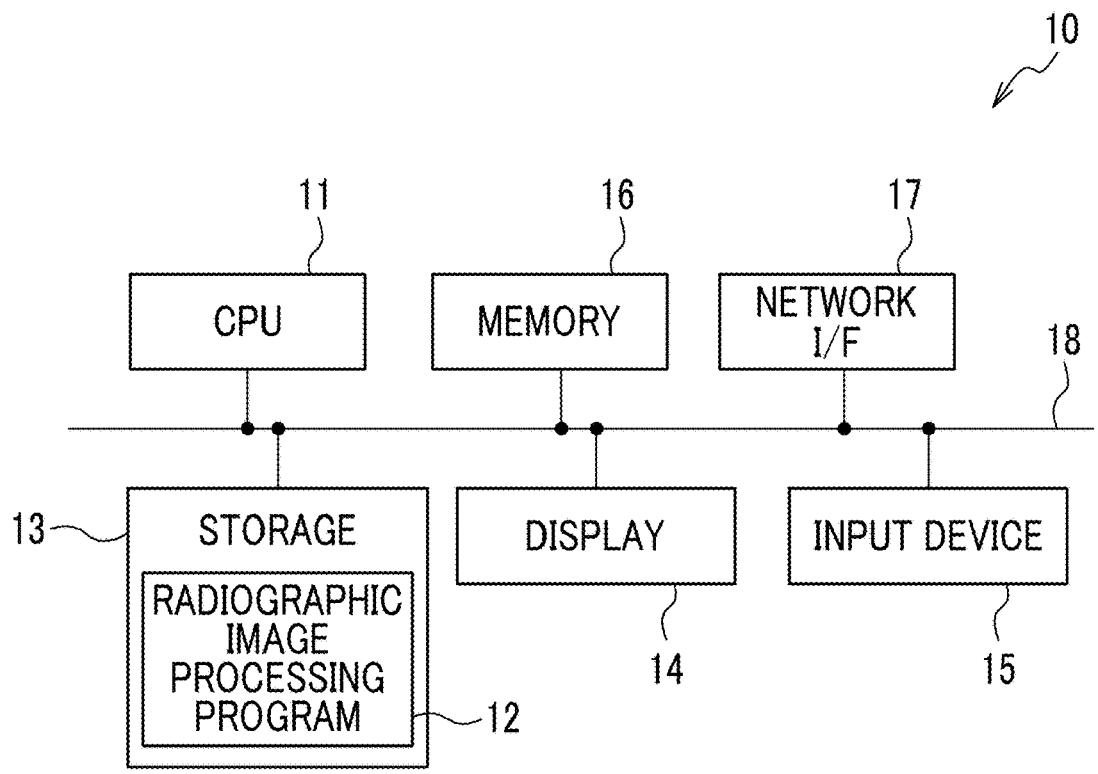
FIG. 2 is a diagram schematically illustrating a configuration of the radiographic image processing device according to the first embodiment.

Next, the radiographic image processing device according to this embodiment will be described. First, the hardware configuration of the radiographic image processing device according to this embodiment will be described with reference to FIG. 2. As illustrated in FIG. 2, the radiographic image processing device 10 is a computer, such as a workstation, a server computer, or a personal computer, and comprises a central processing unit (CPU) 11, a non-volatile storage 13, and a memory 16 as a temporary storage area. In addition, the radiographic image processing device 10 comprises a display 14, such as a liquid crystal display, an input device 15, such as a keyboard and a mouse, and a network interface (I/F) 17 that is connected to a network. The CPU 11, the storage 13, the display 14, the input device 15, the memory 16, and the network I/F 17 are connected to a bus 18. In addition, the CPU 11 is an example of a processor according to the present disclosure.

The storage 13 is implemented by, for example, a hard disk drive (HDD), a solid state drive (SSD), and a flash memory. A radiographic image processing program 12 installed in the radiographic image processing device 10 is stored in the storage 13 as a storage medium. The CPU 11 reads the radiographic image processing program 12 from the storage 13, expands the radiographic image processing program 12 in the memory 16, and executes the expanded radiographic image processing program 12.

In addition, the radiographic image processing program 12 is stored in a storage device of a server computer connected to the network or a network storage so as to be accessed from the outside and is downloaded and installed in the computer forming the radiographic image processing device 10 on demand. Alternatively, the radiographic image processing program 12 is recorded on a recording medium, such as a digital versatile disc (DVD) or a compact disc read only memory (CD-ROM), is distributed, and is installed in the computer forming the radiographic image processing device 10 from the recording medium.

Figure 3:
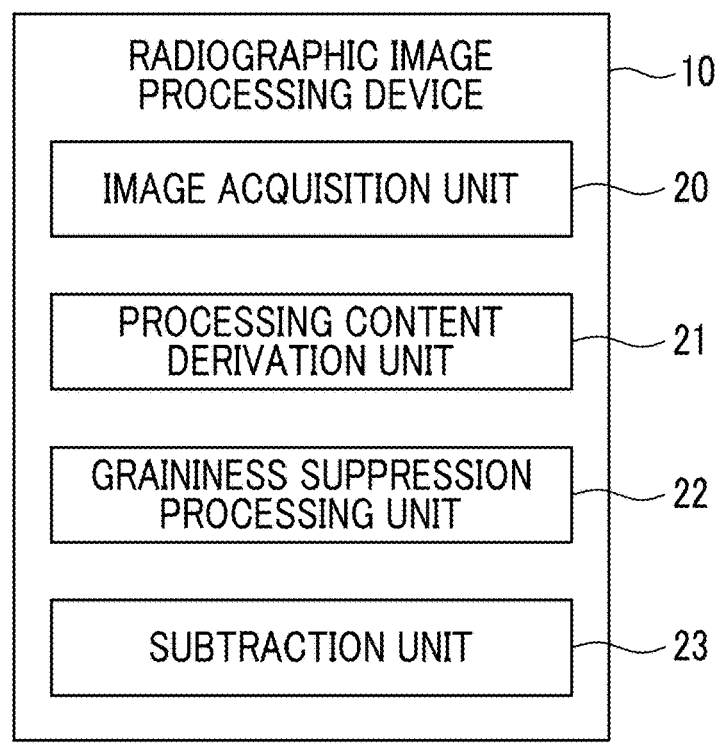
FIG. 3 is a diagram illustrating a functional configuration of the radiographic image processing device according to the first embodiment.

Next, the functional configuration of the radiographic image processing device according to this embodiment will be described. FIG. 3 is a diagram illustrating the functional configuration of the radiographic image processing device according to this embodiment. As illustrated in FIG. 3, the radiographic image processing device 10 comprises an image acquisition unit 20, a processing content derivation unit 21, a graininess suppression processing unit 22, and a subtraction unit 23. Then, the CPU 11 executes the radiographic image processing program 12 to function as the image acquisition unit 20, the processing content derivation unit 21, the graininess suppression processing unit 22, and the subtraction unit 23.

The image acquisition unit 20 directs the imaging apparatus 1 to capture the images of the subject H and acquires the first radiographic images G1 and the second radiographic image G2 which are the front images of the subject H from the first and second radiation detectors 5 and 6. In a case in which the first radiographic image G1 and the second radiographic image G2 are acquired, imaging conditions, such as an irradiation dose of radiation, a tube voltage, and a source-to-image receptor distance (SID), are set. The set imaging conditions are stored in the storage 13.

In addition, the first and second radiographic images G1 and G2 may be acquired by a program different from the radiographic image processing program according to this embodiment. In this case, the first and second radiographic images G1 and G2 are stored in the storage 13, and the image acquisition unit 20 reads the first and second radiographic images G1 and G2 stored in the storage 13 in order to process the first and second radiographic images G1 and G2.

The processing content derivation unit 21 derives the processing content of a first graininess suppression process on the first radiographic image G1 and derives the processing content of a second graininess suppression process on the second radiographic image G2 on the basis of the processing content of the first graininess suppression process.

Here, in this embodiment, the image of the subject H is captured by a one-shot method. In the case of the one-shot method, two radiation detectors 5 and 6 which are stacked with the radiation energy conversion filter 7 interposed therebetween are irradiated with the radiation transmitted through the subject H. Therefore, the second radiation detector 6 farther away from the radiation source 3 is irradiated with a lower dose of radiation than the first radiation detector 5 closer to the radiation source 3. As a result, the second radiographic image G2 has a larger amount of radiation quantum noise and a lower S/N ratio than the first radiographic image G1. Therefore, particularly, it is necessary to perform a graininess suppression process for suppressing graininess caused by quantum noise on the second radiographic image G2.

The processing content derivation unit 21 derives the processing content of the first graininess suppression process on the first radiographic image G1 having a higher S/N ratio of the first radiographic image G1 and the second radiographic image G1. Then, the processing content derivation unit 21 derives the processing content of the second graininess suppression process on the second radiographic image G2 on the basis of the processing content of the first graininess suppression process. Hereinafter, the derivation of the processing content will be described.

An example of the graininess suppression process is a filtering process using a smoothing filter such as a Gaussian filter having a predetermined size of, for example, 3×3 pixels or 5×5 pixels centered on a pixel of interest. However, in a case in which the Gaussian filter is used, the edge of a structure included in the first and second radiographic images G1 and G2 is likely to be blurred. Therefore, in this embodiment, the graininess suppression process is performed using an edge-preserving smoothing filter that suppresses graininess while preventing the blurring of the edge. An example of the edge-preserving smoothing filter is a bilateral filter having, as a weight, a normal distribution in which a weight for a pixel adjacent to the pixel of interest becomes smaller as the pixel becomes further away from the pixel of interest and the weight becomes smaller as the difference in pixel value between the pixel and the pixel of interest becomes larger.

Figure 4:
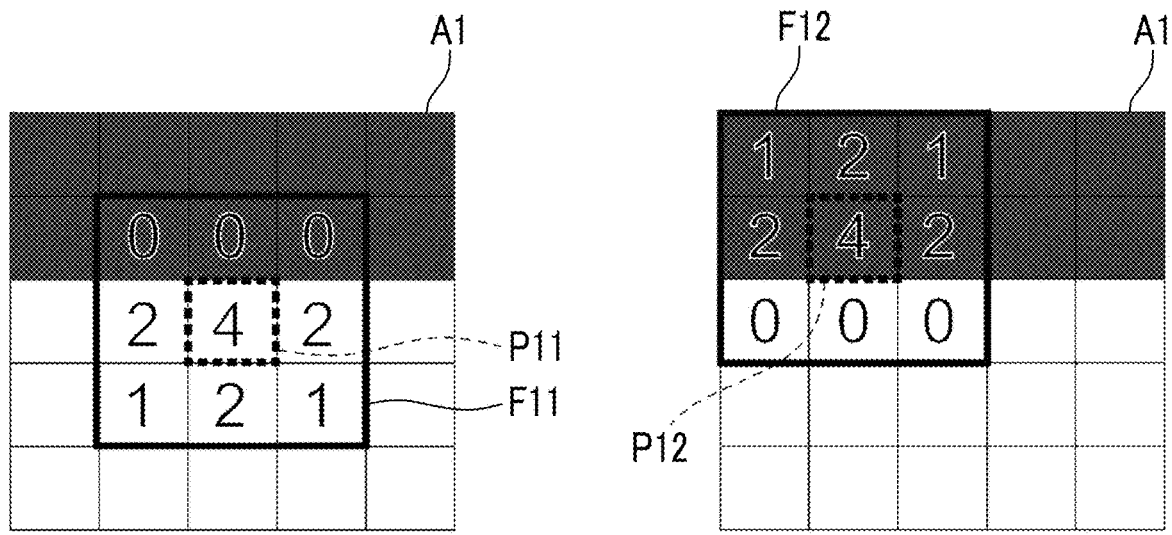
FIG. 4 illustrates a bilateral filter for a first radiographic image.

FIG. 4 is a diagram illustrating an example of the bilateral filter for the first radiographic image G1. In addition, FIG. 4 illustrates two local regions A1 with a size of 5×5 pixels in the vicinity of the edge in the first radiographic image G1 side by side. Further, the two local regions A1 illustrated in FIG. 4 are the same, but the positions of the pixels of interest are different from each other. In the left local region A1 in FIG. 4, a low-density pixel that comes into contact with the boundary of the edge is a pixel of interest P11. As described above, the bilateral filter has, as a weight, the normal distribution in which a weight for a pixel adjacent to the pixel of interest becomes smaller as the pixel becomes further away from the pixel of interest and the weight becomes smaller as the difference in pixel value between the pixel and the pixel of interest becomes larger.

Therefore, the processing content derivation unit 21 determines the size of the bilateral filter on the basis of the difference between the pixel value of the pixel of interest and the pixel value of a pixel around the pixel of interest. For example, as the difference between the pixel value of the pixel of interest and the pixel value of the pixel around the pixel of interest becomes larger, the filter size becomes larger. In addition, the size of the bilateral filter is an example of a processing region according to the present disclosure. Further, the processing content derivation unit 21 determines the weight of the bilateral filter on the basis of the difference between the pixel value of the pixel of interest and the pixel value of the pixel around the pixel of interest. For example, as the difference between the pixel value of the pixel of interest and the pixel value of the pixel around the pixel of interest becomes smaller, a weight for a pixel close to the pixel of interest becomes larger than a weight for a pixel far away from the pixel of interest.

Therefore, for the pixel of interest P11 in the left local region A1 in FIG. 4, the processing content derivation unit 21 derives a 3×3 bilateral filter F11 having weights illustrated on the left side in FIG. 4 as the processing content of the first graininess suppression process.

In the right local region A1 in FIG. 4, a high-density pixel that comes into contact with the boundary of the edge is a pixel of interest P12. Therefore, for the pixel of interest P12 in the right local region A1 in FIG. 4, the processing content derivation unit 21 derives a 3×3 bilateral filter F12 having weights illustrated on the right side in FIG. 4 as the processing content of the first graininess suppression process.

Figure 5:
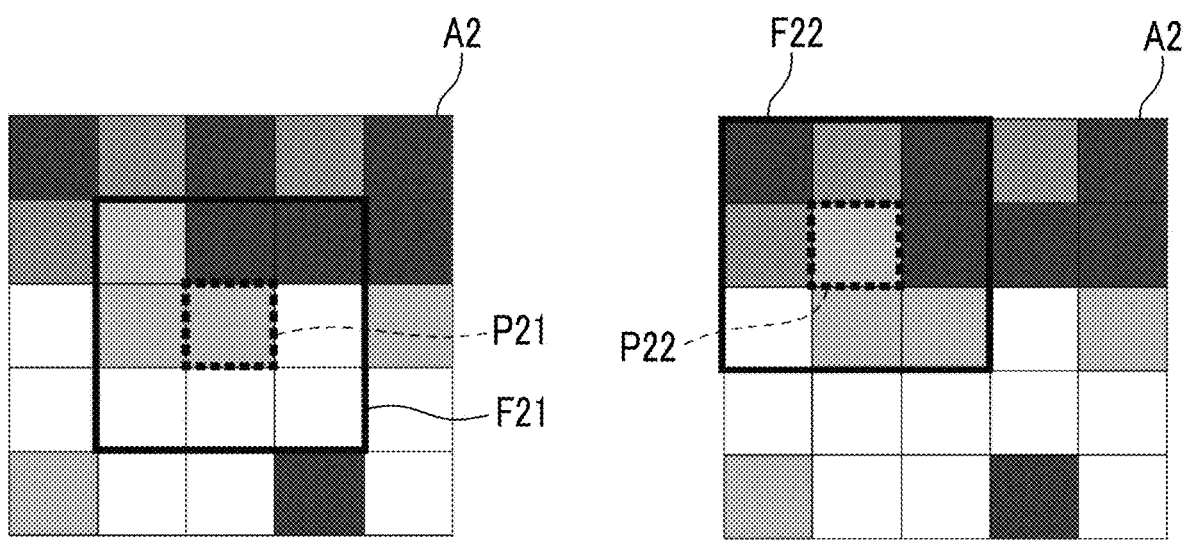
FIG. 5 is a diagram illustrating a local region of a second radiographic image corresponding to a local region of the first radiographic image illustrated in FIG. 4.

FIG. 5 is a diagram illustrating a local region A2 of the second radiographic image which corresponds to the local region A1 of the first radiographic image illustrated in FIG. 4. FIG. 5 illustrates the local region A2 with a size of 5×5 pixels in the vicinity of the edge included in the second radiographic image G2. The local region A2 is located at the same position as the local region A1 of the first radiographic image G1 illustrated in FIG. 4. The two local regions A2 illustrated in FIG. 5 are the same, but the positions of the pixels of interest are different from each other. In the left local region A2 in FIG. 5, a pixel corresponding to the pixel of interest P11 illustrated in the left local region A1 in FIG. 4 is a pixel of interest P21. In the right local region A2 in FIG. 5, a pixel corresponding to the pixel of interest P12 illustrated in the right local region A1 in FIG. 4 is a pixel of interest P22.

Here, the second radiation detector 6 that acquires the second radiographic image G2 is irradiated with a lower dose of radiation than the first radiation detector 5 that acquires the first radiographic image G1. Therefore, the second radiographic image G2 has a larger amount of radiation quantum noise and poorer graininess than the first radiographic image G1. As a result, the edge does not appear clearly in the second radiographic image G2. Further, a low-density pixel is included in a high-density region in the vicinity of the boundary of the edge or a high-density pixel is included in a low-density region due to the influence of quantum noise. Therefore, it is difficult to appropriately determine a bilateral filter for suppressing graininess while preserving the edge from the second radiographic image G2, unlike the first radiographic image G1.

In this case, it is considered to use a smoothing filter such as a Gaussian filter. However, in a case in which the smoothing filter is used, it is difficult to achieve both the suppression of noise and the preservation of the edge. As a result, the edge is buried in noise, which makes it difficult to restore the edge of the structure included in the second radiographic image G2.

Therefore, in this embodiment, the processing content derivation unit 21 derives the processing content of the second graininess suppression process on the second radiographic image G2 on the basis of the processing content of the first graininess suppression process on the first radiographic image G1. That is, the processing content derivation unit 21 derives the processing content of the second graininess suppression process such that the processing content of the second graininess suppression process performed on each pixel of the second radiographic image G2 is the same as the processing content of the first graininess suppression process performed on each pixel of the first radiographic image G1 corresponding to each pixel of the second radiographic image G2. Specifically, the processing content derivation unit 21 derives a bilateral filter that has the same size and weight as the bilateral filter determined for each pixel of the first radiographic image G1 as the processing content of the second graininess suppression process on the second radiographic image G2.

Figure 6:
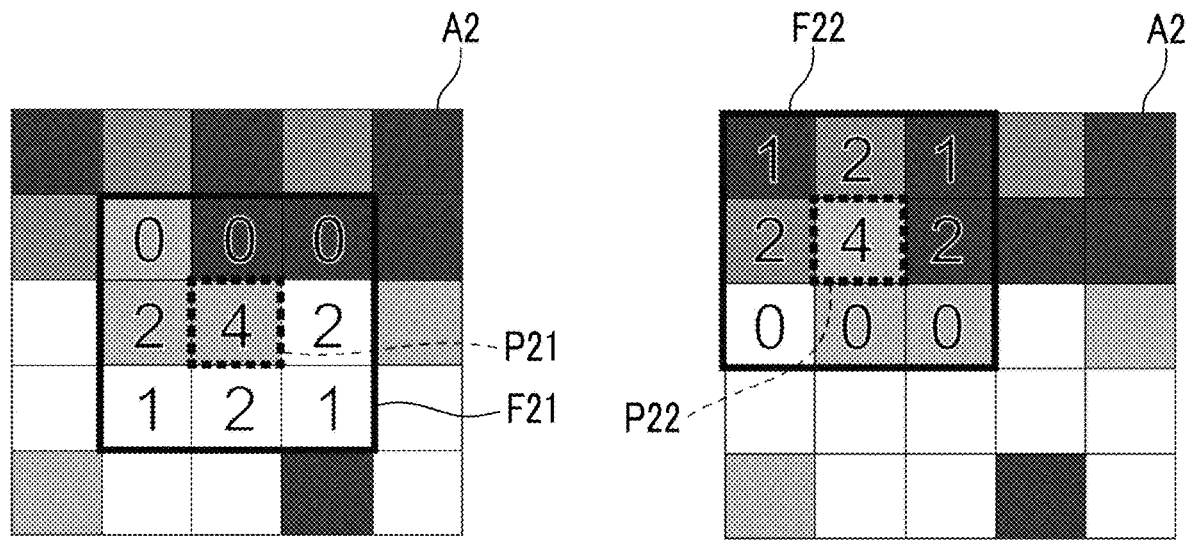
FIG. 6 is a diagram illustrating an example of a bilateral filter for a second radiographic image.

FIG. 6 is a diagram illustrating an example of the bilateral filter for the second radiographic image. In addition, FIG. 6 illustrates a local region A2 with a size of 5×5 pixels in the vicinity of the edge included in the second radiographic image G2 similarly to FIG. 5. As illustrated in FIG. 6, for a pixel of interest P21 in the local region A2 of the second radiographic image G2, the processing content derivation unit 21 derives, as the processing content of the second graininess suppression process, a bilateral filter F21 which has the same size and weight as the bilateral filter F11 derived for the pixel of interest P11 in the local region A1 of the first radiographic image G1.

In addition, for a pixel of interest P22 in the local region A2 of the second radiographic image G2, the processing content derivation unit 21 derives, as the processing content of the second graininess suppression process, a bilateral filter F22 which has the same size and weight as the bilateral filter F12 derived for the pixel of interest P12 in the local region A1 of the first radiographic image G1.

In a case in which the processing content of the second graininess suppression process is derived, it is necessary to associate the pixel positions of the first radiographic image G1 and the second radiographic image G2. Therefore, it is preferable to register the first radiographic image G1 and the second radiographic image G2.

The graininess suppression processing unit 22 performs the graininess suppression process on the first radiographic image G1 and the second radiographic image G2. That is, the graininess suppression processing unit 22 performs the graininess suppression process on the first radiographic image G1 and the second radiographic image G2 on the basis of the processing content derived by the processing content derivation unit 21. Specifically, the graininess suppression processing unit 22 performs the filtering process on the first radiographic image G1 using the bilateral filter derived for the first radiographic image G1. Further, the graininess suppression processing unit 22 performs the filtering process on the second radiographic image G2 using the bilateral filter derived on the basis of the first radiographic image G1.

The subtraction unit 23 performs a subtraction process on the first radiographic image G1 and the second radiographic image G2 subjected to the graininess suppression process using the following Expressions (1) and (2) to derive a soft part image Gs obtained by extracting a soft part of the subject H and a bone part image Gb obtained by extracting a bone part of the subject H. In Expressions (1) and (2), α and β are weighting coefficients.

$$Gs(x,y)=\alpha \cdot G2(x,y)-G1(x,y) \quad (1)$$

$$Gb(x,y)=\beta \cdot G2(x,y)-G1(x,y) \quad (2)$$

Figure 7:
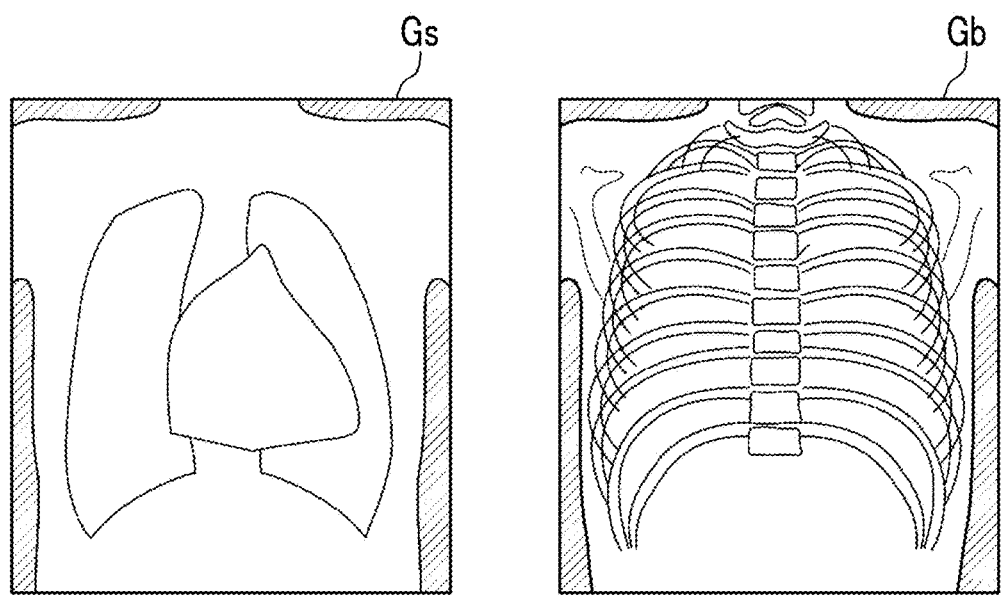
FIG. 7 is a diagram illustrating a soft part image and a bone part image.

FIG. 7 is a diagram illustrating a soft part image and a bone part image. As illustrated in FIG. 7, the soft part image Gs is obtained by extracting the soft part of the subject H. Further, the bone part image Gb is obtained by extracting the bone part of the subject H. The generated soft part image Gs and bone part image Gb are stored in the storage 13 or are displayed on the display 14.

Figure 8:
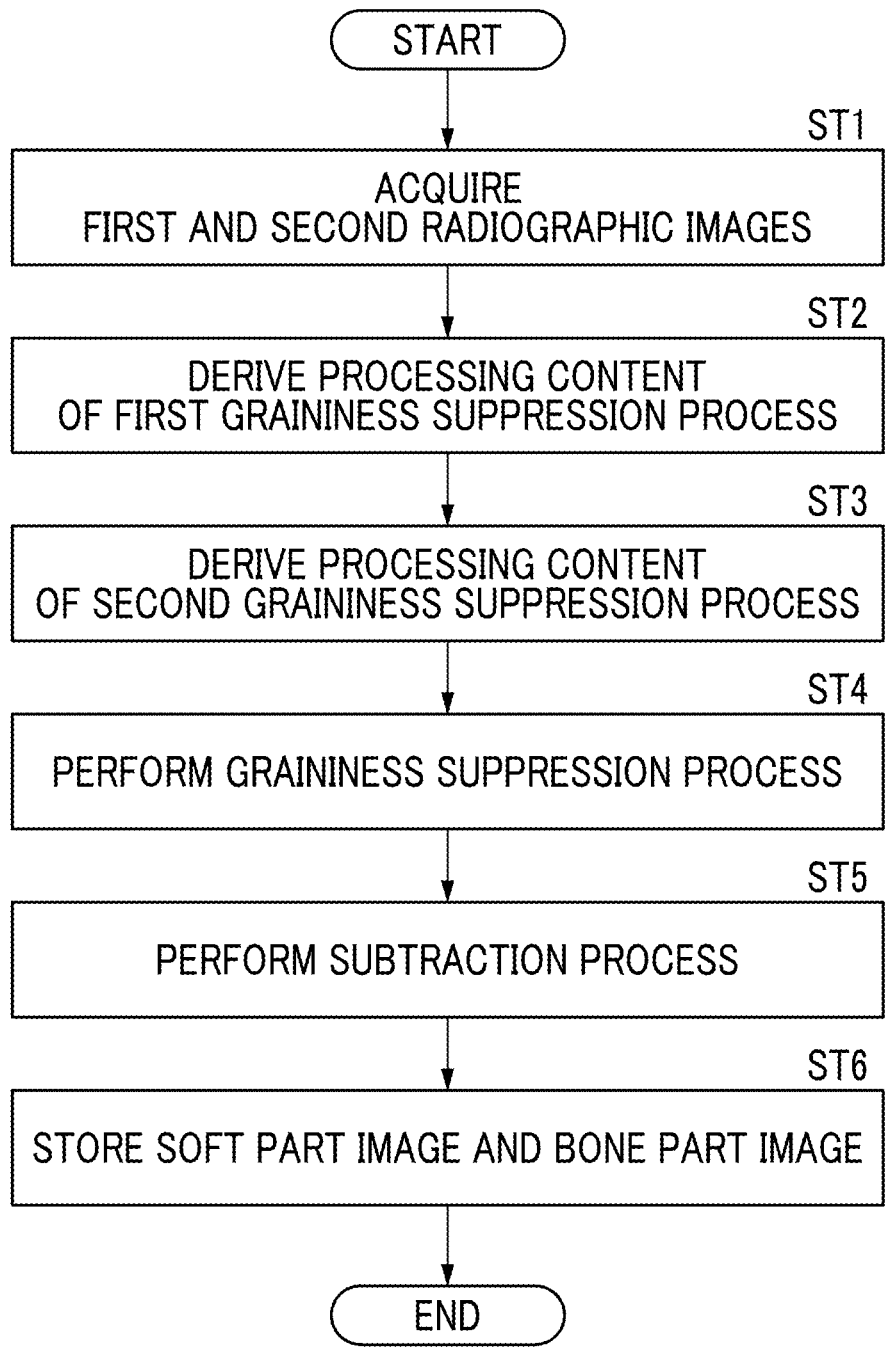
FIG. 8 is a flowchart illustrating a process performed in the first embodiment.

Next, a process performed in the first embodiment will be described. FIG. 8 is a flowchart illustrating the process performed in the first embodiment. In addition, it is assumed that the first and second radiographic images G1 and G2 are acquired by imaging and are then stored in the storage 13. In a case in which an instruction to start the process is input from the input device 15, the image acquisition unit 20 acquires the first and second radiographic images G1 and G2 from the storage 13 (Step ST1). Then, first, the processing content derivation unit 21 derives the processing content of the first graininess suppression process on the first radiographic image G1 (Step ST2). Then, the processing content derivation unit 21 derives the processing content of the second graininess suppression process on the second radiographic image G2 on the basis of the processing content of the first graininess suppression process (Step ST3).

Then, the graininess suppression processing unit 22 performs the graininess suppression process on the first radiographic image G1 and the second radiographic image G2 (Step ST4). Then, the subtraction unit 23 performs the subtraction process using Expressions (1) and (2) (Step ST5). The soft part image Gs and the bone part image Gb are derived by this process. The derived soft part image Gs and bone part image Gb are stored in the storage 13 (Step ST6). Then, the process ends. In addition, instead of or in addition to storing the soft part image Gs and the bone part image Gb, the soft part image Gs and the bone part image Gb may be displayed on the display 14.

As such, in this embodiment, the processing content of the first graininess suppression process on the first radiographic image G1 is derived, and the processing content of the second graininess suppression process on the second radiographic image G2 is derived on the basis of the processing content of the first graininess suppression process. Here, the first radiographic image G1 has a higher edge contrast and less noise than the second radiographic image G2. Therefore, in a case in which the graininess suppression process is performed on the first radiographic image G1 on the basis of the processing content of the first graininess suppression process, it is possible to suppress graininess while preserving the edge. On the other hand, the second radiographic image G2 has a large amount of noise and does not have good graininess. However, in a case in which the graininess suppression process is performed according to the same processing content of the second graininess suppression process as the first graininess suppression process, it is possible to suppress graininess such that the edge is not buried in noise while preserving the edge corresponding to that in the first radiographic image G1. Therefore, it is possible to appropriately suppress the graininess of the radiographic image with a low S/N ratio.

Figure 9:
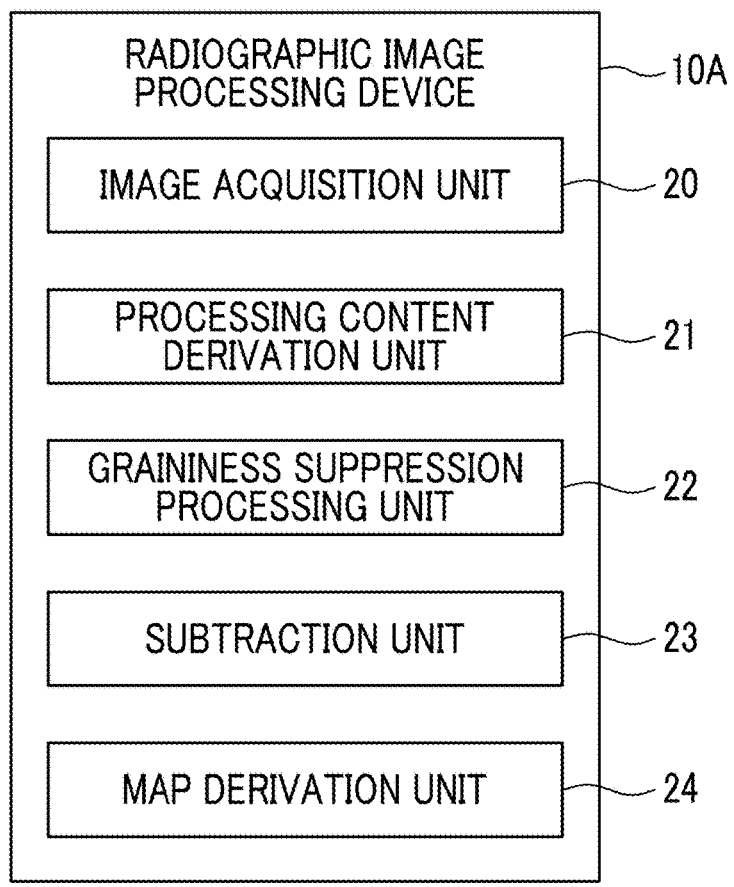
FIG. 9 is a diagram illustrating a functional configuration of a radiographic image processing device according to a second embodiment.

Next, a second embodiment of the present disclosure will be described. FIG. 9 is a diagram illustrating the functional configuration of the radiographic image processing device according to the second embodiment of the present disclosure. Further, in FIG. 9, the same configurations as those in FIG. 3 are denoted by the same reference numerals, and the detailed description thereof will not be repeated. A radiographic image processing device 10A according to the second embodiment differs from the radiographic image processing device according to the first embodiment in that it further comprises a map derivation unit 24 that derives a physical quantity map of the subject H on the basis of at least one of the first radiographic image G1 or the second radiographic image G2 and the processing content derivation unit 21 derives the processing content of the second graininess suppression process on the second radiographic image G2 on the basis of the physical quantity map.

The map derivation unit 24 derives the physical quantity of the subject H. Examples of the physical quantity include the body thickness and bone density of the subject H. In addition, the SID may be used as the physical quantity corresponding to the body thickness. Here, a case where the body thickness is derived as the physical quantity will be described. The map derivation unit 24 derives the body thickness of the subject H for each pixel of the first and second radiographic images G1 and G2 on the basis of at least one of the first radiographic image G1 or the second radiographic image G2. Since the body thickness is derived for each pixel of the first and second radiographic images G1 and G2, the map derivation unit 24 derives a body thickness distribution in at least one of the first radiographic image G1 or the second radiographic image G2. In a case in which the body thickness is derived, the map derivation unit 24 uses the first radiographic image G1 acquired by the radiation detector 5 closer to the subject H. However, the second radiographic image G2 may be used. Further, even in a case in which any one of the images is used, a low-frequency image indicating a low-frequency component of the image may be derived, and the body thickness may be derived using the low-frequency image.

In the second embodiment, assuming that a brightness distribution in the first radiographic image G1 is matched with the distribution of the body thickness of the subject H, the map derivation unit 24 converts the pixel value of the first radiographic image G1 into a thickness using an attenuation coefficient in the soft part of the subject H to derive the body thickness of the subject H. Instead of this, a sensor may be provided in the imaging apparatus 1, and the thickness of the subject H may be measured using the sensor. In addition, the map derivation unit 24 may approximate the body thickness of the subject H with a model, such as a cube or an elliptical column, to derive the body thickness. Further, the map derivation unit 24 may derive the body thickness of the subject H using any method such as the method disclosed in, for example, JP2015-043959A.

Furthermore, in a case in which a bone mineral content is derived as the physical quantity, the map derivation unit 24 derives the bone mineral content using, for example, the method disclosed in JP2019-209027A. In a case in which the method disclosed in JP2019-209027A is used, the map derivation unit 24 derives the bone part image Gb from the first radiographic image G1 and the second radiographic image G2 before the graininess suppression process, using Expression (2). Then, the map derivation unit 24 converts each pixel of the bone part image Gb into a pixel value of the bone part image acquired under the reference imaging conditions to derive the bone mineral content. Specifically, the map derivation unit 24 corrects each pixel value of the bone part image Gb using a predetermined correction coefficient for converting the pixel value of the bone part image into a bone mineral content to derive the bone mineral content.

Here, the contrast of a structure included in the radiographic image to be subjected to the graininess suppression process varies depending on the imaging conditions. Therefore, in a case in which the edge-preserving smoothing process is performed using a bilateral filter, it is necessary to control the intensity of the edge to be preserved according to the imaging conditions. On the other hand, the contrast of the structure included in the body thickness map indicating the body thickness of the subject H and a bone mineral content map is represented by the thickness (mm) or the bone mineral content ($g/cm^2$) that does not depend on the imaging conditions.

Figure 10:
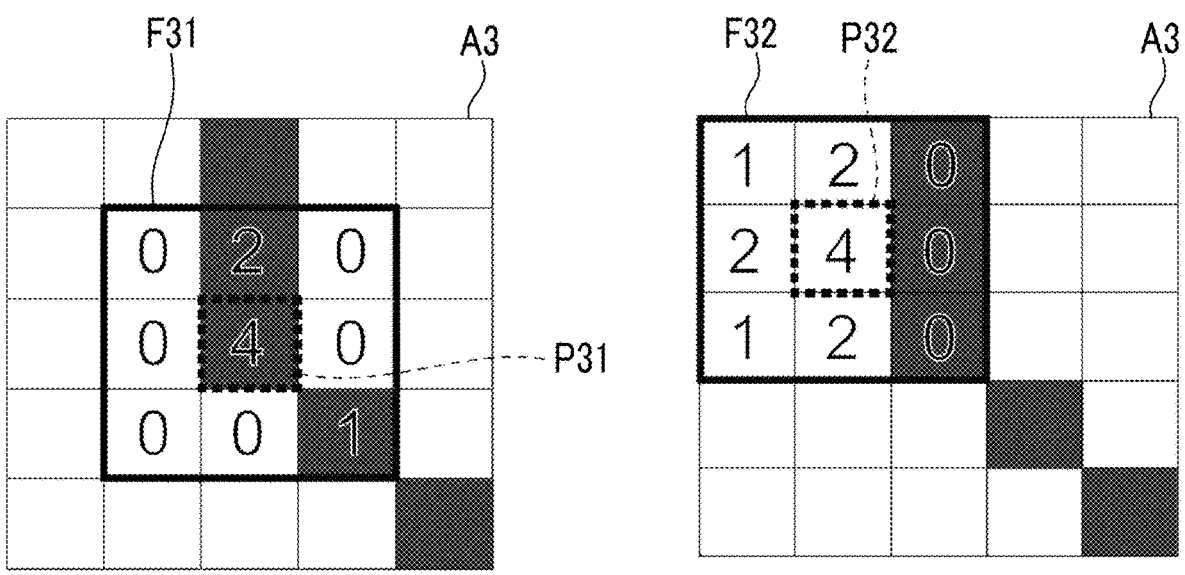
FIG. 10 is a diagram illustrating an example of a bilateral filter for a physical quantity map.

Therefore, in the second embodiment, the processing content derivation unit 21 derives the processing content of the first graininess suppression process on the first radiographic image G1 on the basis of the physical quantity map. FIG. 10 is a diagram illustrating an example of the bilateral filter for the physical quantity map. In addition, FIG. 10 illustrates two local regions A3 with a size of 5×5 pixels in the vicinity of the edge included in the physical quantity map side by side. The two local regions A3 illustrated in FIG. 10 are the same, but the positions of the pixels of interest are different from each other. In the left local region A3 in FIG. 10, a high-density pixel on the edge is a pixel of interest P31. Therefore, for the pixel of interest P31 in the left local region A3 in FIG. 10, a 3×3 bilateral filter F31 having weights illustrated on the left side in FIG. 10 is derived as the processing content of the first graininess suppression process.

In the right local region A3 in FIG. 10, a low-density pixel that comes into contact with the boundary of the edge is a pixel of interest P32. Therefore, for the pixel of interest P32 in the right local region A3 in FIG. 10, a 3×3 bilateral filter F32 having weights illustrated on the right side in FIG. 10 is derived as the processing content of the first graininess suppression process.

In the second embodiment, the processing content derivation unit 21 derives the same bilateral filter as the bilateral filter determined for each pixel of the first radiographic image G1 as the processing content of the second graininess suppression process on the second radiographic image G2. That is, in the local region of the second radiographic image G2 which corresponds to the local region A3 of the first radiographic image G1, for the pixel corresponding to the pixel of interest P31 in the local region A3, a bilateral filter that has the same size and weight as the bilateral filter F31 is derived as the processing content of the second graininess suppression process. Further, in the second radiographic image G2, for the pixel corresponding to the pixel of interest P32 in the local region A3 of the first radiographic image G1, a bilateral filter that has the same size and weight as the bilateral filter F32 is derived as the processing content of the second graininess suppression process.

Figure 11:
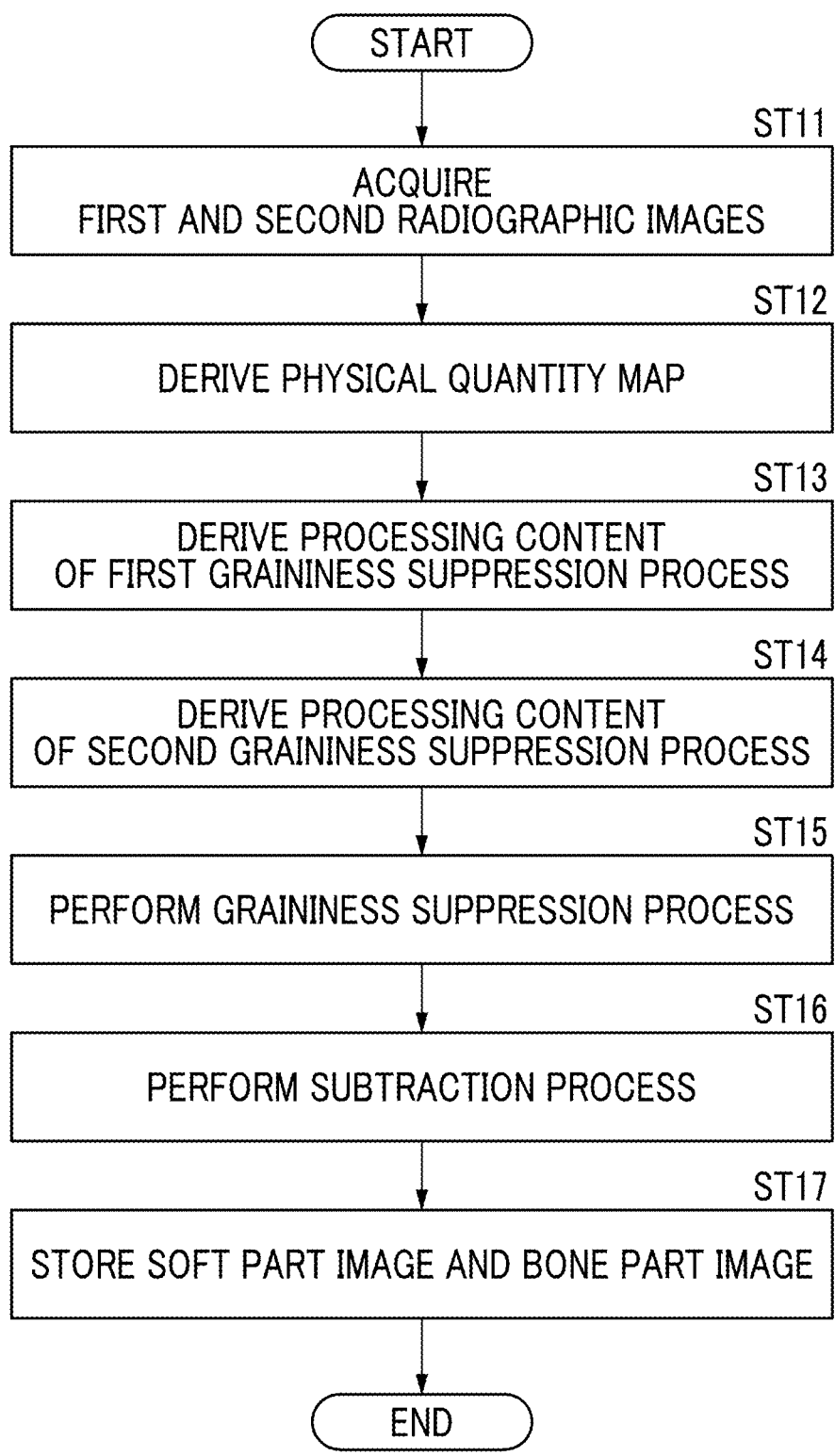
FIG. 11 is a flowchart illustrating a process performed in the second embodiment.

Next, a process performed in the second embodiment will be described. FIG. 11 is a flowchart illustrating the process performed in the second embodiment. In addition, it is assumed that the first and second radiographic images G1 and G2 are acquired by imaging and are then stored in the storage 13. In a case in which an instruction to start the process is input from the input device 15, the image acquisition unit 20 acquires the first and second radiographic images G1 and G2 from the storage 13 (Step ST11). Then, the map derivation unit 24 derives the physical quantity map of the subject H on the basis of at least one of the first radiographic image G1 or the second radiographic image G2 (Step ST12).

Then, first, the processing content derivation unit 21 derives the processing content of the first graininess suppression process on the first radiographic image G1 on the basis of the physical quantity map (Step ST13). Then, the processing content derivation unit 21 derives the processing content of the second graininess suppression process on the second radiographic image G2 on the basis of the processing content of the first graininess suppression process (Step ST14).

Then, the graininess suppression processing unit 22 performs the graininess suppression process on the first radiographic image G1 and the second radiographic image (Step ST15). Then, the subtraction unit 23 performs the subtraction process using Expressions (1) and (2) (Step ST16). The soft part image Gs and the bone part image Gb are derived by this process. The derived soft part image Gs and bone part image Gb are stored in the storage 13 (Step ST17). Then, the process ends. In addition, instead of or in addition to storing the soft part image Gs and the bone part image Gb, the soft part image Gs and the bone part image Gb may be displayed on the display 14.

Here, the contrast of the structure included in the first and second radiographic images G1 and G2 to be subjected to the graininess suppression process varies depending on the imaging conditions. Therefore, in a case in which the edge-preserving smoothing process is performed using the bilateral filter and there is a structure desired to be preserved without being smoothed, it is necessary to adjust the intensity of the edge to be preserved according to the imaging conditions. On the other hand, in the body thickness map indicating the body thickness of the subject H or the bone mineral content map indicating the bone mineral content of the subject H, the pixel value is represented by the thickness (mm) or the bone mineral content ($g/cm^2$). Therefore, the contrast of the structure included in the map does not change depending on the imaging conditions. Therefore, in a case in which there is a structure desired to be preserved without being smoothed, it is possible to set the intensity of the edge to be preserved on the basis of a value that does not depend on the imaging conditions such as a difference in body thickness or a difference in bone density between the structure desired to be preserved and a surrounding structure. For example, in a case in which it is desired to leave a signal of a blood vessel structure having a diameter of 1 mm and the body thickness map is used, the intensity of the edge to be preserved may be set such that a structure having a body thickness difference of 1 mm or more from a surrounding structure is preserved.

In the second embodiment, the physical quantity map of the subject H is derived, and the processing content of the second graininess suppression process on the second radiographic image G2 is derived on the basis of the physical quantity map. Therefore, it is possible to derive the processing content of the first graininess suppression process and the second graininess suppression process without being affected by a change in the contrast of the structure in the image due to a change in the imaging conditions.

In each of the above-described embodiments, the bilateral filter is used as the edge-preserving smoothing filter. However, the present disclosure is not limited thereto. The graininess suppression process may be performed using a non-local means filter that performs weighting on the basis of the similarity between the pixel of interest and a neighborhood region of any pixel in the image. In this case, it is also possible to suppress graininess while preserving the edge.

Further, in each of the above-described embodiments, the filtering process using the edge-preserving smoothing filter is performed as the graininess suppression process. However, the present disclosure is not limited thereto. One or more pixels that are within a predetermined distance from the pixel of interest and have a pixel value whose difference from the pixel value of the pixel of interest is equal to or greater than a predetermined threshold value may be specified in the first radiographic image G1, and a smoothing process on the pixel of interest and the specified pixel may be derived as the processing content of the first graininess suppression process. In this case, the processing content of the second graininess suppression process may be derived such that the pixel of interest and the specified image are smoothed in the second radiographic image G2.

In addition, in each of the above-described embodiments, the graininess suppression process is performed by the filtering process. However, the present disclosure is not limited thereto. A function, such as a mathematical expression for performing the graininess suppression process, may be derived as the processing content of the graininess suppression process, and the graininess suppression process may be performed on the first and second radiographic images G1 and G2 using the derived function.

Further, in each of the above-described embodiments, the graininess suppression process is performed on the first radiographic image G1 and the second radiographic image G2. However, the present disclosure is not limited thereto. Multi-resolution conversion, such as wavelet conversion, may be performed on the first radiographic image G1 and the second radiographic image G2 to generate a plurality of band images having different frequency bands, and the processing content of the first graininess suppression process and the processing content of the second graininess suppression process may be derived for the band images of each frequency band. The first graininess suppression process and the second graininess suppression process may be performed on the band images of each frequency band for the first and second radiographic images G1 and G2, respectively. Frequency synthesis may be performed on the processed band images to derive the first and second radiographic images G1 and G2 subjected to the graininess suppression process.

Further, in each of the above-described embodiments, the first and second radiographic images G1 and G2 are acquired by the one-shot method. However, the first and second radiographic images G1 and G2 may be acquired by a so-called two-shot method that performs imaging twice.

In the case of the two-shot method, the dose of radiation in a second imaging operation is lower than the dose of radiation in a first imaging operation in order to reduce the dose of exposure to the subject H. Therefore, of the first and second radiographic images G1 and G2, one radiographic image (here, the second radiographic image G2) has a larger amount of noise than the first radiographic image G1. Therefore, even in a case in which the first and second radiographic images G1 and G2 are acquired by the two-shot method, the processing content of the second graininess suppression process on the second radiographic image G2 may be derived on the basis of the processing content of the first graininess suppression process on the first radiographic image G1 as in the above-described embodiments.

Further, in the case of the two-shot method, the position of the subject H included in the first radiographic image G1 and the second radiographic image G2 is likely to be shifted by the body movement of the subject H. Therefore, it is preferable to perform the process according to this embodiment after aligning the position of the subject in the first and second radiographic images G1 and G2. For example, the method disclosed in JP2011-255060A can be used as the positioning process. For example, the method disclosed in JP2011-255060A generates a plurality of first band images and a plurality of second band images indicating structures having different frequency bands for each of first and second radiographic images G1 and G2, acquires the amount of positional deviation between the corresponding positions in the first band image and the second band image of the corresponding frequency band, and registers the first radiographic image G1 and the second radiographic image G2 on the basis of the amount of positional deviation.

Further, in the above-described embodiments, the energy subtraction process is performed using the radiographic images acquired by the system that captures the radiographic images of the subject H using the first and second radiation detectors 5 and 6. However, the present disclosure may also be applied to a case in which the first and second radiographic images G1 and G2 are acquired using a storage phosphor sheet instead of the radiation detectors. In this case, the first and second radiographic images G1 and G2 may be acquired by stacking two storage phosphor sheets, irradiating the storage phosphor sheets with radiation transmitted through the subject H such that the radiographic image information of the subject H is accumulated and recorded on each storage phosphor sheet, and photoelectrically reading the radiographic image information from each storage phosphor sheet. In addition, the two-shot method may also be used in a case in which the first and second radiographic images G1 and G2 are acquired using the storage phosphor sheets.

Further, the radiation in each of the above-described embodiments is not particularly limited. For example, α-rays or γ-rays can be applied in addition to the X-rays.

In the above-described embodiments, for example, the following various processors can be used as a hardware structure of processing units performing various processes, such as the image acquisition unit 20, the processing content derivation unit 21, the graininess suppression processing unit 22, the subtraction unit 23, and the map derivation unit 24. The various processors include, for example, a CPU which is a general-purpose processor executing software (program) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

Furthermore, specifically, an electric circuit (circuitry) obtained by combining circuit elements, such as semiconductor elements, can be used as the hardware structure of the various processors.

What is claimed is:

1. A radiographic image processing device comprising:
at least one processor,
wherein the processor is configured to
    acquire a first radiographic image and a second radiographic image that include a same subject and have different S/N ratios,
    derive a body thickness map indicating a body thickness or a bone mineral content map of the subject on the basis of at least one of the first radiographic image or the second radiographic image,
    derive a processing content of a first graininess suppression process on the first radiographic image having a higher S/N ratio of the first radiographic image and the second radiographic image on the basis of a difference between a body thickness of a pixel of interest and a body thickness of a pixel around the pixel of interest in the first radiographic image based on the body thickness map, or on the basis of a difference between a bone mineral content of the pixel of interest and a bone mineral content of the pixel around the pixel of interest in the first radiographic image based on the bone mineral content map,
    derive a processing content of a second graininess suppression process on the second radiographic image on the basis of the processing content of the first graininess suppression process, and
    perform a graininess suppression process on the second radiographic image on the basis of the processing content of the second graininess suppression process.

2. The radiographic image processing device according to claim 1,
wherein the processing content of the second graininess suppression process performed on each pixel of the second radiographic image is the same as the processing content of the first graininess suppression process performed on each pixel of the first radiographic image corresponding to each pixel of the second radiographic image.

3. The radiographic image processing device according to claim 1,
wherein the processor is configured to derive a processing region, in which the first graininess suppression process is performed on the pixel of interest, as the processing content of the first graininess suppression process on the basis of the difference.

4. The radiographic image processing device according to claim 3,
wherein the processor derives a weight for a pixel in the processing region as the processing content of the first graininess suppression process on the basis of the difference.

5. The radiographic image processing device according to claim 1,
wherein the first radiographic image and the second radiographic image are acquired on the basis of radiation that is for energy subtraction and has different energy distributions.

6. A radiographic image processing method comprising:
acquiring a first radiographic image and a second radiographic image that include a same subject and have different S/N ratios;
deriving a body thickness map indicating a body thickness or a bone mineral content map of the subject on the basis of at least one of the first radiographic image or the second radiographic image;
deriving a processing content of a first graininess suppression process on the first radiographic image having a higher S/N ratio of the first radiographic image and the second radiographic image on the basis of a difference between a body thickness of a pixel of interest and a body thickness of a pixel around the pixel of interest in the first radiographic image based on the body thickness map, or on the basis of a difference between a bone mineral content of the pixel of interest and a bone mineral content of the pixel around the pixel of interest in the first radiographic image based on the bone mineral content map;
deriving a processing content of a second graininess suppression process on the second radiographic image on the basis of the processing content of the first graininess suppression process; and
performing a graininess suppression process on the second radiographic image on the basis of the processing content of the second graininess suppression process.

7. A non-transitory computer-readable storage medium that stores a radiographic image processing program that causes a computer to execute:
a procedure of acquiring a first radiographic image and a second radiographic image that include a same subject and have different S/N ratios;
a procedure of deriving a body thickness map indicating a body thickness or a bone mineral content map of the subject on the basis of at least one of the first radiographic image or the second radiographic image;
a procedure of deriving a processing content of a first graininess suppression process on the first radiographic image having a higher S/N ratio of the first radiographic image and the second radiographic image on the basis of a difference between a body thickness of a pixel of interest and a body thickness of a pixel around the pixel of interest in the first radiographic image based on the body thickness map, or on the basis of a difference between a bone mineral content of the pixel of interest and a bone mineral content of the pixel around the pixel of interest in the first radiographic image based on the bone mineral content map;
a procedure of deriving a processing content of a second graininess suppression process on the second radiographic image on the basis of the processing content of the first graininess suppression process; and
a procedure of performing a graininess suppression process on the second radiographic image on the basis of the processing content of the second graininess suppression process.

8. The radiographic image processing device according to claim 1,
   wherein the pixel of interest is a pixel in a structure desired to be preserved in the first radiographic image and the second radiographic image, and
   wherein the processor is configured to derive the content of the first graininess suppression process in accordance with an intensity of an edge to be preserved.

9. The radiographic image processing device according to claim 1,
   wherein the processor is configured to set an intensity of an edge to be preserved on the basis of the difference.

10. The radiographic image processing device according to claim 9,
   wherein the processor is configured to perform an edge-preserving smoothing process as the graininess suppression process on the basis of the set intensity of the edge.

* * * * *